(12) United States Patent
Boiteau et al.

(10) Patent No.: US 10,520,458 B2
(45) Date of Patent: Dec. 31, 2019

(54) IDENTIFICATION METHOD FOR ELECTROCHEMICAL TEST STRIPS

(71) Applicant: AgaMatrix, Inc., Salem, NH (US)

(72) Inventors: Charles Boiteau, Carlisle, MA (US); Martin Forest, Nashua, NH (US); Sridhar Iyengar, Salem, NH (US); Baoguo Wei, Salem, NH (US)

(73) Assignee: AgaMatrix, Inc., Salem, NH (US)

( * ) Notice: Subject to any disclaimer, the term of this patent is extended or adjusted under 35 U.S.C. 154(b) by 644 days.

(21) Appl. No.: 14/987,872

(22) Filed: Jan. 5, 2016

(65) Prior Publication Data

US 2016/0209349 A1 Jul. 21, 2016

Related U.S. Application Data

(63) Continuation of application No. 12/248,195, filed on Oct. 9, 2008.

(60) Provisional application No. 60/978,978, filed on Oct. 10, 2007.

(51) Int. Cl.
*G01N 27/30* (2006.01)
*G01N 33/487* (2006.01)
*G01N 27/327* (2006.01)

(52) U.S. Cl.
CPC ....... *G01N 27/307* (2013.01); *G01N 27/3272* (2013.01); *G01N 27/3274* (2013.01); *G01N 33/48771* (2013.01)

(58) Field of Classification Search
CPC .......... C12Q 1/00; C12Q 1/001; C12Q 1/004; C12Q 1/005; C12Q 1/006; C12Q 1/26; C12Q 1/34; C12Q 1/54; G01N 27/48; G01N 27/26; G01N 27/327–3274;
(Continued)

(56) References Cited

U.S. PATENT DOCUMENTS

| 4,714,874 A | 12/1987 | Morris et al. |
| 5,526,120 A | 6/1996 | Jina et al. |
| 6,773,671 B1 | 8/2004 | Lewis et al. |

(Continued)

FOREIGN PATENT DOCUMENTS

| EP | 1288653 A1 | 3/2003 |
| NO | 2009049015 A2 | 4/2009 |

OTHER PUBLICATIONS

Extended European Search Report dated Sep. 17, 2014 from corresponding European Application No. 08837648.8.
(Continued)

*Primary Examiner* — Maris R Kessel
(74) *Attorney, Agent, or Firm* — Larson & Anderson, LLC

(57) ABSTRACT

The present invention provides a method and apparatus for creating test strips that may be identified based on differences in electrical conduction or resistance between contact point on the test strip. This is achieved by creating a base test strip with contact points that may be connected to other contact points by an electrical connection. These base test strips may be modified to create a difference in electrical conductivity between contact points, or a contact point may be eliminated. This modification can be used to distinguish different types of test strips based on electrical signature. Additionally, the base test strip may be created such that multiple modifications are possible to distinguish numerous characteristics of test strips.

13 Claims, 3 Drawing Sheets

(58) Field of Classification Search
CPC ........... G01N 33/487; G01N 33/48707; G01N 33/48771; G01N 27/307; A61B 5/05; A61B 5/14532
See application file for complete search history.

(56) References Cited

U.S. PATENT DOCUMENTS

| | | | |
|---|---|---|---|
| 6,800,488 B2 | 10/2004 | Khan et al. | |
| 6,827,829 B2 | 12/2004 | Kawanaka et al. | |
| 2004/0200721 A1* | 10/2004 | Bhullar | C01N 33/48771 204/403.01 |
| 2004/0244151 A1* | 12/2004 | Sakata | G01N 33/48771 23/306 |
| 2005/0016845 A1 | 1/2005 | Groll et al. | |
| 2005/0279647 A1 | 12/2005 | Beaty | |
| 2006/0144704 A1 | 7/2006 | Ghesquiere et al. | |
| 2006/0231417 A1 | 10/2006 | Harding et al. | |
| 2007/0110615 A1 | 5/2007 | Neel et al. | |
| 2008/0105024 A1* | 5/2008 | Creaven | G01N 21/274 73/1.02 |
| 2008/0267823 A1* | 10/2008 | Wang | C12Q 1/006 422/68.1 |
| 2009/0029479 A1* | 1/2009 | Docherty | C12Q 1/004 436/149 |
| 2009/0030617 A1* | 1/2009 | Schell | G01N 33/48771 702/19 |
| 2009/0288964 A1* | 11/2009 | Jung | A61B 5/14532 205/792 |

OTHER PUBLICATIONS

Medical Devices and Systems, The Biomedical Engineering Handbook, 3rd Edition, published in 2006 by CRC Press, p. 66-6.
Description for "Test Strip", Wikipedia, 1 page, Retrieved from "https://en.wikipedia.org/w/index.php?title+Test_strip&oldid=545872552" on May 19, 2017.
Description of "Glucose Meter", Wikipedia, 11 pages, Retreived from "https://en.wikipedia.org/w/index.php?title=Glucose_meter&oldid=766681532" on May 19, 2017.
Description of "Lot", Industrial Safety Dictionary, May 10, 2004, 3 pages, Retreived on Jun. 7, 2017 from https://translate.googleusercontent.com/translate_c?depth=1&hl=...04%26categoryId%3D50304&usg=ALkJrhh4CyPSEhS6Qg6z1VU15MXP0ODrDw.
Description of "Batch process", Industrial Safety Dictionary, May 10, 2004, 2 pages, Retreived from https://translate.googleusercontent.com/translate_c?act=url7depth...2380%26categoryId%3D42380&usg=ALkJrhj84_HkvlJuFFboAdEIZBK1TIwq5g on Jun. 7, 2017.

* cited by examiner

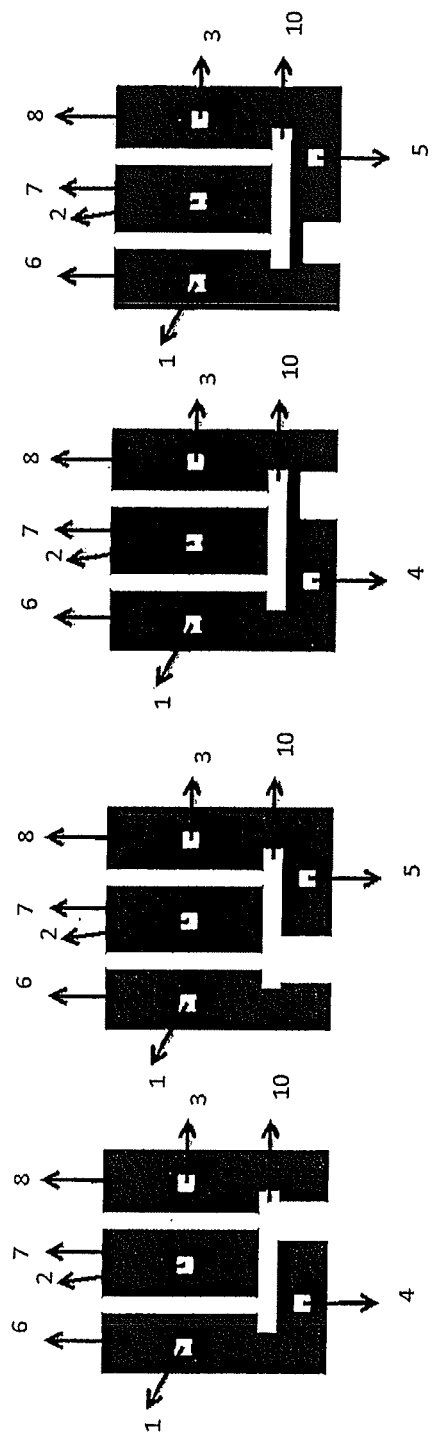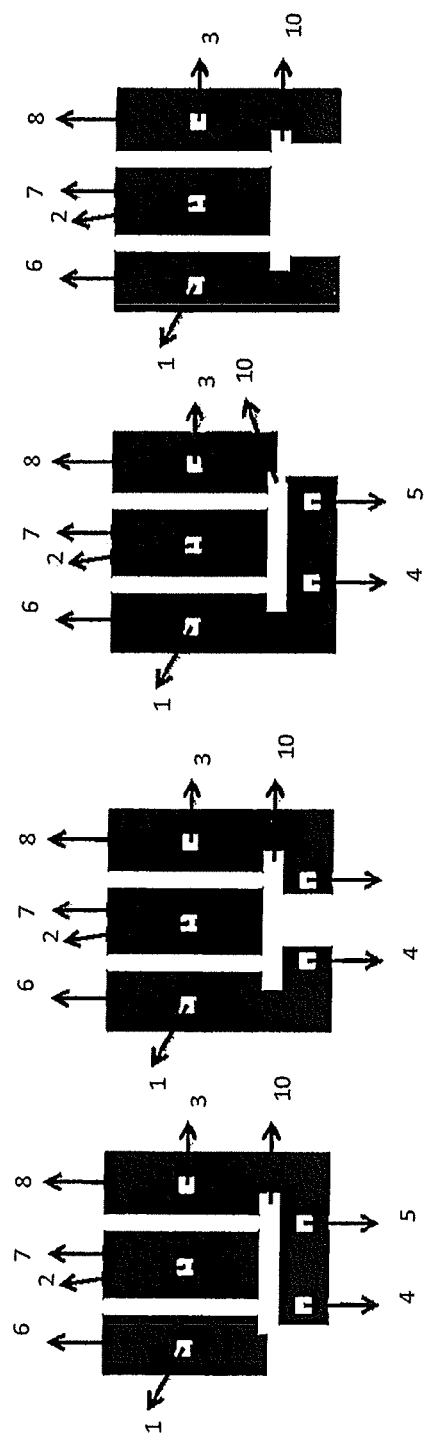

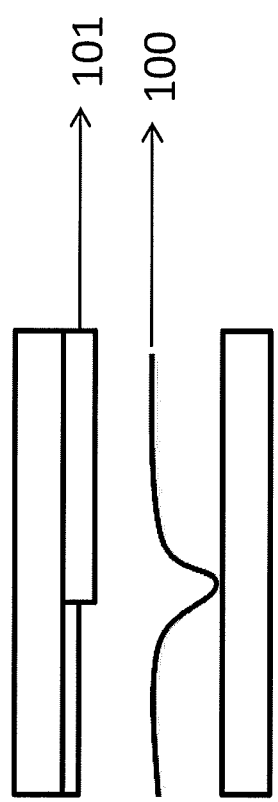
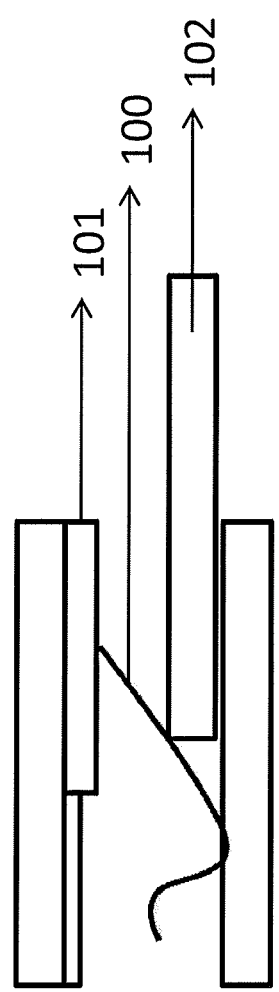

IDENTIFICATION METHOD FOR ELECTROCHEMICAL TEST STRIPS

BACKGROUND OF THE INVENTION

This application relates to a method for identification of electrochemical test strips to distinguish one type or one lot of test strips from another using a meter such as that which is used with the test strip to assess the amount of an analyte, such as glucose, in a sample.

Small-volume, single-use disposable test strips are in common use in application such as the self-measurement of blood glucose levels by diabetics. These test strips contain electrodes and reagents, and in use are associated with a meter that provides the circuitry to analyze a sample placed in the meter. In order to maintain appropriate quality control and comply with different regulatory standards, strips made for sales in different geographical regions may be made in a different and distinguishable manner.

SUMMARY OF THE INVENTION

The present invention provides a method of making a plurality of test strips where the test strips are part of either a base test strip group or one or more modified test strip groups. The modified test strip groups are distinguishable from the base group. According to the method, a base test strips are created where the base test strips have a region of electrically conductive material and a plurality of accessible contact points connected to one another by said electrically conductive material. These contact points interact with an analyte test meter, such as a blood glucose test meter.

Some of the base test strips are modified by physical removal of electrically conductive material or complete removal of at least one contact point to create a group of modified test strips. The test strips within the modified test strip group are distinguishable from the base test strip due to a difference in electrical conductivity/resistance between the contact points. Additional groups of modified test strips may be created by removal of electrically conductive material or complete removal of at least one contact point from some of the base test strips, to a different extent, such that the additional modified test strip group is distinguishable from the base test strip and the first modified test strip group.

The test strips may be assigned to groups based on meeting or not meeting a specification. To do this, representatives of a lot of base test strips are tested to determine whether the lot meets a specification. The lot of test strips is then assigned to a group based on meeting the specification and the test strips assigned to a modified test strip group are modified to indicate the group.

This method creates a family of test strips including a base test strip group and at least one modified test strip group. The base test strips have a region of electrically conductive material and a plurality of accessible contact points connected to one another by said electrically conductive material. The modified test strip are base test strips modified by physical removal of electrically conductive material or at least one contact point. The modified test strip is distinguishable from the base test strip due to a difference in electrical conductivity/resistance between the contact points. Additional modified test strip groups may also be created where a portion of the base test strip is modified by removal of electrically conductive material or at least one contact point and the additional modified test strip group is distinguishable from both the base test strip and the first modified test strip group. Test strips within the family may be assigned to a group based on whether representative samples of a base test strip lot meet a specification.

BRIEF DESCRIPTION OF THE DRAWINGS

FIGS. 2-9 illustrate embodiments of a modified test strip of the invention.

FIG. 10A illustrates a strip port connector.

FIG. 10B illustrates a strip port connector with a strip inserted.

DETAILED DESCRIPTION OF THE INVENTION

Figure 1:
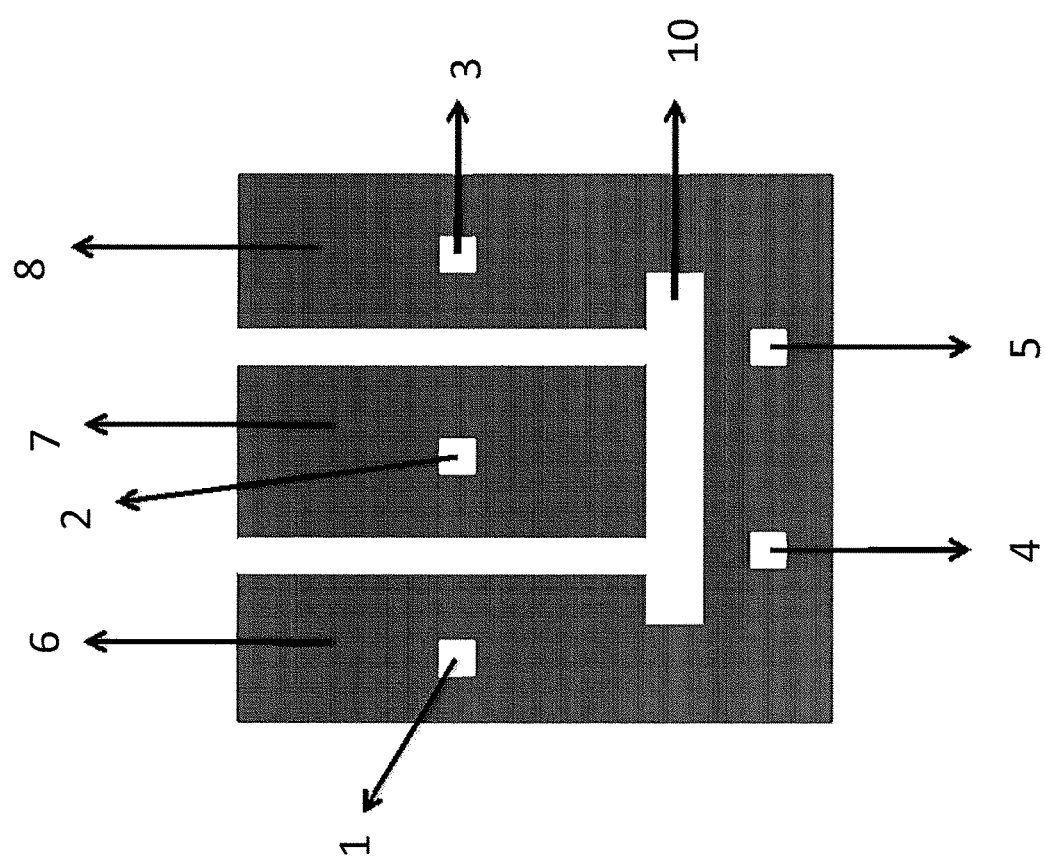
FIG. 1 illustrates an embodiment of a base test strip of the invention.

The present application provides a new approach to the preparation of strips that are part of identifiable groups. These groups may be based on different geographical regions, they may be used to differentiate manufacturers (for example where one brand uses multiple manufacturing sources) or they may be used to differentiate the time of manufacture, thus becoming a type of hard-coded expiration date. In addition, the approach of the invention can be used to distinguish a strip designed for one type of analyte (such as glucose) from another type of analyte (such as cholesterol) such that a multi-function meter will perform the correct analysis with information provided from the strip, not the user.

A further benefit of the present invention is that the encoding for identification of the strips can be applied after a quality control check has been run such that strips can be directed into groups as a final step in manufacturing, rather than requiring a separate manufacturing process for each group of strips. Thus, in one example, strips that meet very high quality control standards can be identified in the method of the invention for use with a meter that does not require a calibration code (a no-code meter), while strips manufactured in the same initial process that do not meet the rigid standards for uniformity but are otherwise acceptable can be identified for use in meters that require a calibration code for the particular lot of the test strips. This eliminates wastage, thus controlling the costs of the strips. Uniformity of test strips within a lot is an example of a "specification" on which assignment to groups can be based.

Once the strips have been assigned to a group, the strips are packaged and may be labeled to indicate the characteristics of the group. For example, the group may be labeled to indicate type of analyte, type of meter, whether a calibration code is necessary, and/or geographic region.

The invention operates by using notches or holes cut into defined locations in a test strip to interrupt initially formed electrical connections. FIG. 1 shows a connection end of a test strip prior to the formation of notches. In the illustrated embodiment, there are 5 points on the strip (labeled 1-5) where electrical contact can be made via 5 pins from the strip port connector (SPC, not shown). In actual practice there can be more contact points, or fewer contact points than the five shown here. In preferred embodiments, the contact points are arranged in two or more groups, each at a different depth from the end of the test strip. The exact alignment of these rows as a single line is not required, although it may make it easier to design the contacts in the SPC. In common usage, the contact points 1, 2 and 3 also serve as the electrical connectors to for example to working and counter electrodes and a fill detection electrode. The numerals 6, 7 and 8 in the figure refer to the leads from such structures which may or may not be electrically isolated from one another. For example, leads 6 and 8 can both be in contact with a common electrode or one leg can be in contact with the sample space and an active measurement electrode (working or counter) and the other may simply be a conductive region that is not involved in measurement. Lead 7 is then in contact with the other of the measurement electrodes. The specific arrangement of the leads is not critical to the present invention.

In the figures of this application, the contact points are shown as white squares for clarity. The contact points do not have to be separate structures, however, and are generally just locations on the conductive surface of the test strip that are accessible to probes on the SPC.

The strip as depicted in FIG. 1 also includes a region of insulating material 10 which separates leads 6, 7 and 8 from each other, and which partially separate the two rows of contact points. This region is suitably an underlying insulating substrate where the conductive material is not disposed.

The presence and/or absence of electrical continuity between electrical contact points on the strip is be probed by the meter to ensure uniqueness of the strip. Pairs of points and/or combinations of pairs of points can be used to arrive at strip designs that are unique with respect to the electrical features.

FIGS. 2-9 show different notching patterns that can be used to define different strip identification groups. In FIG. 2, the notch extends into the insulating region 10, eliminates contact point 5 and disconnects 3 from every other point on the test strip. Thus, measurement of the connection (for example as a resistance measurement) between points 1 and 4 would show connection (low resistance) while that between 3 and 4 would show no connection (high/infinite resistance) comparable to that observed between point 2 and point 4. Point 2 in this figure is always electrically isolated, and therefore measurements using point 2 can, if desired be used as a kind of control indicator of the no connection. Tests with a connector where point 3 was eliminated would show comparable yet distinguishable results. In FIG. 3, the notch eliminates contact point 4 and disconnects 1 from every other point. Thus, this test strip would produce results parallel to but different from the results of the strip of FIG. 2. The notch can be long enough to extend into the insulating region 10 as shown in FIGS. 2 and 3 or it can extend only partially into the end of the strip as show in FIGS. 4 and 5. In FIG. 4, the notch eliminates contact point 5 but does not disconnect 3 from every other contact point. Rather, the resistance between 4 and 3 is dependent on the width of the conductive portion, and thus can be used as an indicator of the place and extent of notching. Similarly, in FIG. 5, the notch eliminates contact point 4 but does not disconnect 1 from every other contact point. The resistance between 1 and 5 is dependent on the width of the conductive portion.

In FIG. 6, the notch breaks the continuity between 1 and 5. In FIG. 7, the notch breaks the continuity between 4 and 5. In FIG. 8, the notch breaks the continuity between 3 and 5. In FIG. 9, the notch eliminates points 4 and 5. In this configuration, one of the leads, for example lead 6, does not make contact with the sample chamber, it just serves the back of the strip. Thus, electrical continuity is maintained between points 1 and 3.

As noted above, alteration in the width of the conductive path is achieved by notching out portions of the strip as a physical removal of the entire thickness of the strip. Alternatively, this can be achieved by laser ablation to remove the conductive material between the contact points. Thus in a general sense the invention provides a postprocessing step in which conductive material is removed to modify the electrical continuity between selected ones of a plurality of contact points in order to provide for a multiplicity of possible group identifications.

The notching can be complete (100%) so as to completely sever the electrical connection such that no current can flow across (as shown in FIG. 2), or it may be incomplete. The lower the width of the conductive path, the greater the resistance. The variable extent of notching (eg: 25%, 50%, 75%) will alter the resistance correspondingly. One example is shown in (FIGS. 4,5). Isolation of one conductive point can be achieved by ablating a ring around that contact point. In the case of an ablated ring around a contact point, the diameter of the ring can be used define the extent of notching so that a large diameter ring (overlapping both the insulating region and the end of the strip) will result in complete notching while smaller diameter rings can be used to produce different levels of resistance. Similar results can be achieved by cutting holes (rather than end notches) that surround one of the contact points. Indeed, a hole may be preferred to an end notch in cases of an incomplete cut where variable resistance is utilized, since alignment is not critical as long as the hole does not overlap with either the end of the strip or the insulating region 10. These techniques provide examples of removal of electrically conductive material.

The use of variable resistance adds great versatility to the identification capabilities of the invention because the same structure, with a limited number of contact points, can produce many different and distinguishable configurations each of which can be assessed without any change in the design of the SPC.

The strips of the invention with conductive material removed to define identifiable groups can be used in combination with mechanical features on the strip and meter to prevent improper insertion (i.e. upside down) of the test strip. Features of this type are known in the art, for example from U.S. Pat. No. 5,526,120, which is incorporated herein by reference. In addition, the SPC can have a post in a position corresponding to a notch which will be received in the notch when an appropriate strip is inserted in the SPC and which will prevent insertion of a strip with a notch in an inappropriate position for the particular meter.

Where a notch is used that extends to the end of the strip, the presence or absence of a notch in a particular position can also be used to interact with a switch mechanism, which can be used to activate the meter if a correctly coded strip is inserted, or to set the operation of the meter depending on the type of strip (as indicated by the position of the notch) inserted. As depicted in FIG. 10A, the strip port connector may contain a deflectable switch part 100 and a fixed switch contact 101. When a strip 102 is inserted that is not notched in alignment with this switch, the deflectable switch portion 100 is deflected to make contact with the fixed switch contact 101 as show in FIG. 10B. When the strip is notched in alignment with the switch, however, no deflection occurs.

What is claimed is:

1. A method of making a plurality of test strips, wherein said test strips are part of a base test strip group or a modified test strip group distinguishable from the base group comprising:

creating a plurality of base test strips, each base test strip having a region of electrically conductive material, a plurality of accessible contact points connected to one another by said electrically conductive material, and one end configured for insertion into a testing apparatus, and assigning each of the plurality of base test strips to a lot of test strips;

testing base test strips representative of a first lot of base test strips to determine whether the first lot of base test strips meets a specification;

assigning the first lot of base test strips to a group based on meeting the specification or not meeting the specification; and modifying the first lot of base test strips assigned to the group to create a first modified test strip group by creating a full thickness notch that extends from the end configured for insertion into a testing apparatus into the region of electrically conductive material, wherein information about the first modified test strip group is conveyed by location, width, and length of the notch.

2. The method of claim 1 further comprising the step of creating a second modified test strip group by modifying a second lot of base test strips by creating a full thickness notch that extends from the end configured for insertion into a testing apparatus into the region of electrically conductive material, wherein information about the second modified test strip group is conveyed by location, width, and length of the notch.

3. The method of claim 2, wherein creating a second modified test strip group comprises:

testing base test strips representative of the second lot of base test strips to determine whether the second lot of base test strips meets a second specification;

assigning the strips of the second lot of base test strips to a second group based on meeting the second specification; and modifying the second lot of base test strips to indicate the second group.

4. The method of claim 3 wherein the specification indicates that the test strips are of a suitable quality as to be used without calibration.

5. The method of claim 3 where said test strips are used to detect glucose.

6. The method of claim 1 where said test strips are configured to detect glucose.

7. The method of claim 1 wherein the base test strips have contact points arranged in two or more groups, each at a different depth from an end of the test strip.

8. The method of claim 7 wherein the base test strips consist of five contact points, arranged in two rows, with a first row having two contact points at a lesser depth from the end of the test strip and a second row with three contact points at a greater depth from the end of the test strip;

a region of insulating material separates one of the contact points in the second row from the other two contact points in the second row; and said insulating material partially separates the first row and second row of contact points.

9. The method according to claim 1, wherein creation of the notch includes removal of at least a portion of a contact point.

10. The method according to claim 1, wherein creation of the notch includes removal of a contact point.

11. The method according to claim 1, wherein creation of the notch includes removal of test strip material beyond the region of electrically conductive material.

12. The method according to claim 11, wherein test strip material includes insulating material.

13. The method according to claim 1, wherein creating a notch results in a change in resistance across the region of electrically conductive material.

* * * * *